United States Patent [19]

Reed

[11] Patent Number: 4,476,115

[45] Date of Patent: Oct. 9, 1984

[54] ANALGESIC COMPOSITION AND METHOD OF TREATING SUBDERMAL PAIN

[76] Inventor: Raymond E. Reed, P.O. Box 1127, Carefree, Ariz. 85377

[21] Appl. No.: 510,566

[22] Filed: Jul. 5, 1983

[51] Int. Cl.$^3$ .................. A61K 31/60; A61K 31/165; A61K 31/415; A61K 33/04

[52] U.S. Cl. .................................... 424/164; 424/230; 424/273 R; 424/324

[58] Field of Search ............ 424/164, 230, 324, 273 R

[56] References Cited

U.S. PATENT DOCUMENTS

| | | | |
|---|---|---|---|
| 4,012,508 | 3/1977 | Burton | 424/235 |
| 4,036,228 | 7/1977 | Theevwes | 424/14 |
| 4,107,330 | 8/1978 | Sheffner | |
| 4,126,681 | 11/1978 | Reller | 424/234 |

OTHER PUBLICATIONS

Scheuplein, Journal of Investigative Dermatology, vol. 67, pp. 31–33, Jul. 1976.

Shaw et al., British Medical Journal, vol. 283, pp. 875–876, Oct. 1981.

Primary Examiner—Stanley J. Friedman

[57] ABSTRACT

Analgesics applied to the skin together with or subsequent to the application of a non-toxic water-soluble sulfite exhibit enhanced effectiveness for relieving subdermal pain.

11 Claims, No Drawings

ANALGESIC COMPOSITION AND METHOD OF TREATING SUBDERMAL PAIN

This invention deals with the relief of pain in mammals and pertains more specifically to the relief of internal pain of the type that occurs in muscles, joints, appendages and other parts including tissues and organs that are supported by the skeletal framework of the body.

It has been found that the topical application of non-toxic water-soluble sulfites in combination with analgesic drugs to the epidermal layers of the stratum corneum (the skin barrier; also called the non-vascular, stratified epithelium) is effective to provide skin penetration by the analgesic drug and relief of subdermal pain. Unlike the stratum corneum the subdermal layers are involved in the vascular system and its vessels such as the arteries, capillaries, veins, nerves, and lymphatics. The sympathetic and central nervous systems play vital roles in the initiation and relief of pain through nerve centers distributed throughout the organ known as skin.

Analgesic drugs such as aspirin and the like are usually administered orally and less frequently by percutaneous injection using hypodermic needles or intravenous systems for administration. Simple topical application of the drug followed by absorption through the unbroken skin is usually found to be ineffective, in part because the rate of absorption or penetration through the skin is too slow to be effective and because the molecular size of the analgesics is quite large. It has been proposed to enhance the rate of penetration by means of water and an aprotic solvent such as dimethyl sulfoxide. Scheuplein, J.Investig. Dermatology, Vol. 67, 31-38 (1976). However, the absorption of dimethylsulfoxide along with the drug produces undesirable side effects, including inflammation and soreness of the skin as well as foul breath and body odor which persists for several days. It has also been taught in Sheffner U.S. Pat. No. 4,107,330 that application of thioglycolic acid to the surface of the skin increases its permeability for treatment of acne. However, thioglycolic acid, like other mercaptans, has obnoxious odors, it poses toxicity problems and is known to be an irritant. Further, thioglycolic acid is unstable and subject to aerial oxidation when topically applied; this can affect the efficiency of this compound for improving the permeability of the skin. It has also been proposed to adhere to the skin a reservoir containing a medicament with a microporous membrane to control the rate of application of the medicament. Shaw et al., Brit. Med. J., Vol. 283, 875-6 (1981).

It has now been found that penetration of an analgesic drug through the skin, that is, percutaneous absorption of the analgesic is painlessly enabled or greatly enhanced by topical application to the skin of a composition in accordance with the present invention. The invention consequently comprises a composition for treatment of subdermal pain by topical application to the skin comprising a mixture of an analgesic drug with a water-soluble non-toxic sulfite, and the method of treating subdermal pain in a mammal which comprises applying an analgesic drug topically to the skin adjacent to the pain simultaneously or sequentially with the application thereto of an aqueous solution of a water-soluble non-toxic sulfite.

Among the sulfites which can be used in the invention are those containing such cations as alkali and alkaline earth metals, ammonium, and amines, e.g., mono-, di-, and tri-alkanolamine, etc.; the sulfites of sodium, potassium, ammonium, and mono-, di-, and tri-ethanolamines are preferred. Properly formulated, the sulfites are odorless, stable, non-toxic, non-irritating, non-sensitizing and do not initiate any significant undesirable side effects. Anhydrous sulfite salts free from water of crystallization are preferred when the composition of the invention is provided in dry solid form for storage or shipment.

Among the analgesic drugs which can be employed in the present invention are the salicylates (particularly aspirin and sodium salicylate), phenacetin, acetaminophen, acetanilid, antipyrine, aminopyrine, and phenylbutazone. Many commercially available analgesics include combinations of two or more individual analgesic drugs and are suitable for use in the present invention. In practicing the invention, the location to which the combination of sulfite and analgesic is to be applied is determined by the long practiced technique of medical doctors and lay people: pain centers are located by making digital probes in the general area of the body that is basic to the subject's problem. If real pain is present, the individual will react involuntarily when the digital pressure probe strikes a pain center. The mechanism for this reflex action is based on a stimulus (digital pressure) activating the afferent and efferent nerves which initiate a physical response in the form of muscular contractions in the tissues surrounding the pain center.

The sulfite is applied to the skin near the pain center in the form of an aqueous solution having a pH of approximately 2.0 to 9.0 and a concentration of 2 to 9%, preferably 2 to 8% by weight. It may be applied to the skin before or during application to the skin of the desired analgesic. Preferably both are present in a single aqueous medium when it is applied to the skin, resulting in simultaneous application.

The relative proportions of analgesic drug and of sulfite are not critical and may vary over a wide range. In general, the weight ratio of sulfite to analgesic may vary from 2:1 to 15:1 and is preferably from 5:1 to 12:1 in the case of mixed compositions containing both ingredients. Such compositions can be prepared in anhydrous form, either in the form of pastes, when one of the ingredients is a liquid, or in the form of a finely divided solid (which may be formed into tablets with a suitable binder), for storage and shipment, suitable for dissolution in water or alcohol or water-alcohol mixtures immediately prior to use. Because analgesics are commonly dispensed as pills with measured dose levels and because sulfites in granular and powdered form may be easily converted to measured "dosage" pills, a single pill is the simple approach to the combination required to practice the invention. The compositions may also be provided in the form of aqueous solutions, emulsions or dispersions containing the sulfite at the desired concentration, as set forth above. If desired, thickening or gelling agents may also be present to gel or to increase the viscosity of the solution, emulsion or dispersion, and ethyl alcohol may be added to increase solubility of certain analgesics.

In use, the aqueous solution or dispersion containing the sulfite at a concentration of 2 to 9% by weight is applied at ambient temperature (20°-37° C.) directly to the skin or to a bandage or other absorptive material which is then placed directly in contact with the skin; the analgesic, if not already present, is then applied. In either case a wrapping or covering is important both to minimize evaporation of the aqueous medium and to minimize aerial oxidation of the sulfite, and avoid premature oxidation of the reduced skin keratin, and, in the case of low viscosity solutions or dispersions, to prevent flow and maintain the composition in the desired location. The area of skin with which the composition is in contact is also not critical and may vary from about 2 to about 20 square inches or more. The composition is preferably applied to the skin as close to the pain as possible, and the area of application depends upon the size and location of the pain area. When treating pain in a hand or finger, an impervious plastic or rubber glove can be worn to maintain the composition comprising analgesic and aqueous sulfite in contact with the skin and to occlude air, resulting in increased effectiveness of the composition for relieving pain. Complete immersion in the composition of the area of skin close to the source of the pain makes it possible to use a smaller quantity of composition than would otherwise be the case. Dosages are the same as for oral administration or higher; substantially complete percutaneous or transdermal absorption of the analgesic in the present invention is believed to occur within a few hours of administration, usually within 20–30 minutes. Alternatively, the analgesic may be withheld and applied separately to the same area of skin, either in anhydrous form or in the form of an aqueous solution, paste or gel, after the solution of sulfite has been in contact with the skin for a sufficient time, usually at least 10 to 30 minutes, to bring about what is believed to be substantial reduction of the disulfide bonds in the skin keratin.

After the end of the treatment the treated area of the skin is simply allowed to remain exposed to the atmosphere; this results in rapid oxidation of any residual sulfite and of the reduced keratin and restoration of the skin to its original condition.

The location of nerve centers involved in the pain syndrome and their utilization as targets for the application of the analgesic-reducing agent composition give rise to significant benefits. Pain relief is realized promptly during application. Long existing pains due to trauma and pain of recent origin respond rapidly to the treatment as does arthritic pain. Not only does pain relief develop rapidly but in practically all cases the relief is permanent. Exceptions deal with subjects with existing bone diseases such as osteoporosis and osteoarthritis type conditions. Osteoporosis is defined as a bone disease characterized by increasing porosity and brittleness of the bones with age. Osteoarthritis is defined as a slowly progressive, degenerative joint disease found mainly in elderly people. Depending on the history of these afflictions semipermanent relief is realized with many subjects.

Inherent in the use of the sulfite-analgesic composition is the prompt relief of topical and subcutaneous pain during its application. Unlike the historic use of needles and various physical gadgets for skin penetration of drugs for pain relief the use of the compositions described, due to the absence of trauma, is a painless relaxing experience. The following examples will serve to illustrate more fully the nature of the present invention without serving as a limitation upon its scope.

EXAMPLE 1

A dry powder mix of 5 g anhydrous sodium sulfite and 0.65 g of aspirin was prepared and packaged in a sealed plastic envelope for dry storage. For use, the contents of the envelope were dissolved in 95 g water to produce an aqueous solution containing approximately 5% sodium sulfite.

EXAMPLE 2

A composition was prepared as described in Example 1 except that the amount of sodium sulfite was 7.5 g and the mixture was dissolved in about 92 g of water to produce an aqueous solution containing approximately 7.5% sodium sulfite.

EXAMPLE 3

A composition was prepared as described in Example 1 except that there was substituted for the aspirin 1.2 g lysine acetyl salicylate (Aspegic).

EXAMPLE 4

A composition was prepared as described in Example 1 except that acetaminophen (Tylenol) was substituted for the aspirin in the same amount.

EXAMPLE 5

A composition was prepared by dissolving 5 g anhydrous sodium sulfite in 85 g water, then mixing with the solution 10 ml of a 10% by weight water solution of triethanolamine salicylate. Anhydrous Na sulfite salts are desirable because of their stability.

Each of the foregoing compositions, when applied to the skin of a mammal in an amount of 12 ml over an area of 4.5 sq. in. in a layer of absorbent cotton and covered with a water impervious plastic sheet held in place by adhesive tape sealing its margins, or covered with an elastic adhesive bandage or other occlusive material resulted within 30 to 40 minutes in marked reduction of pain previously present in the patient, as evidenced by greatly increased mobility of the patient and reduction in stiffness. No. appreciable reduction in pain was produced by the application of controls from which the reducing agent was omitted, and only slight reduction in pain was produced by other controls in which the analgesic was omitted while retaining the sulfite.

EXAMPLE 6

A soft mouth riding horse, was suffering from pain caused by ring bone of the right front foreleg. This animal had not put this foot down flat on the ground for several weeks. He had developed a limp in the leg when he moved.

A spiral wet bandage (gauze) saturated with a 5% sodium sulfite aqueous solution plus powered aspirin (20 grains) dispersed in 5 fluid ounces of the sulfite solution was wrapped around the leg from the hoof to the knee. An Elastoplast covering bandage to protect the bandaged leg was then applied.

Within 30 minutes the horse put his foot down flat.

By the next morning the pain had obviously been dissipated and the horse, on his own initiative, went into a full gallop. Many months later there was still no indication of recurrence of pain and the horse was being frequently ridden.

EXAMPLE 7

A 4 year old thoroughbred race horse exhibited two bowed tendons in his front legs. The left bowed tendon was treated with the following solution: 1 fluid oz. of a 10% aqueous solution of anhydrous sodium sulfite plus 5 fluid oz. of a 10% aqueous triethanolamine salicylate lotion product. The two solutions were combined with thorough mixing. A 5 yard by 4 inch absorbent cotton roll type bandage was saturated with the solution and applied to the left tendon. An Elastoplast bandage and a roll type blanket material were then applied to the bandaged leg. After two hours the bandages were removed and a substantial improvement in the tendon was noted along with a reduction of the pain level.

EXAMPLE 8

A third horse was treated for sore tendons by substantially the same procedure as in Example 7. He had developed an erratic gait. A substantial reduction in swelling and pain was realized.

I claim:

1. A composition for treatment of subdermal pain by topical application to the skin comprising a mixture of (1) an analgesic drug selected from the group consisting of salicylates, phenocetin, acetaminophen, acetanilid, antipyrine, amino-pyrine, phenylbutazone and mixtures thereof with (2) a water-soluble non-toxic sulfite, the weight ratio of sulfite to analgesic drug being from 2:1 to 15:1.

2. A composition as claimed in claim 1 including in addition an aqueous solvent for said sulfite, the concentration of said sulfite being from 2 to 9% by weight.

3. A composition as claimed in claims 1 or 2 in which said analgesic is a salicylate.

4. A composition as claimed in claims 1 or 2 in which said analgesic is triethanolamine salicylate.

5. A composition as claimed in claims 1 or 2 in which said analgesic is aspirin.

6. A composition as claimed in claims 1 or 2 in which said analgesic is acetaminophen.

7. A composition as claimed in claims 1 or 2 in which said sulfite is sodium sulfite.

8. A composition as claimed in claims 1 or 2 in which said analgesic is a salicylate and said sulfite is sodium sulfite.

9. The method of treating subdermal pain in a mammal which comprises applying an analgesic drug selected from the group consisting of salicylates, phenocetin, acetaminophen, acetanilid, antipyrine, aminopyrine, phenylbutazone and mixtures thereof topically to the skin adjacent to the pain simultaneously or sequentially with the application thereto of an aqueous solution of a water-soluble non-toxic sulfite, the concentration of said sulfite being from 2 to 9% by weight and the ratio of said sulfite to said analgesic drug being from 2:1 to 15:1 by weight.

10. The method as claimed in claim 9 in which said analgesic is a salicylate.

11. The method as claimed in claims 9 or 10 in which said sulfite is sodium sulfite.

* * * * *